United States Patent [19]

Garnier et al.

[11] Patent Number: 4,951,854
[45] Date of Patent: Aug. 28, 1990

[54] BACKUP-PROOF FLUID DISTRIBUTION APPARATUS

[75] Inventors: Didier Garnier, Oraison; Max Giusti, Manosque, both of France

[73] Assignee: EBIM, Manosque Cedex, France

[21] Appl. No.: 270,018

[22] Filed: Nov. 14, 1988

[30] Foreign Application Priority Data

Nov. 13, 1987 [FR] France ................................ 87 15715

[51] Int. Cl.$^5$ ................................................ B05B 7/24
[52] U.S. Cl. .................................... 222/644; 222/630; 239/338; 261/78.2
[58] Field of Search ....................... 261/DIG. 17, 78.2; 239/307, 338, 343, 346, 369–370; 222/630, 638–639, 642, 644–646, 647, 648, 3

[56] References Cited

U.S. PATENT DOCUMENTS

| | | | |
|---|---|---|---|
| 3,027,097 | 3/1962 | Gleason et al. | 239/318 |
| 4,427,004 | 1/1984 | Miller | 128/200.21 |
| 4,658,985 | 4/1987 | Madsen et al. | 222/1 |
| 4,671,435 | 6/1987 | Stout et al. | 222/646 |

FOREIGN PATENT DOCUMENTS

| | | |
|---|---|---|
| 579769 | 6/1933 | Fed. Rep. of Germany . |
| 2531977 | 1/1977 | Fed. Rep. of Germany ... 261/DIG. 17 |
| 606998 | 6/1926 | France . |
| 825469 | 3/1938 | France . |
| 1552806 | 1/1969 | France . |
| 98034 | 1/1978 | Japan .......................... 261/DIG. 17 |

Primary Examiner—Michael S. Huppert
Attorney, Agent, or Firm—Burns, Doane, Swecker & Mathis

[57] ABSTRACT

Apparatus for the distribution of fluid materials, notably liquids such as oils and essential oils, perfumes, and the like, which are typically at least somewhat corrosive vis-a-vis injection heads for the dispensing thereof, includes a distribution nozzle, the geometry and mode of operation of which prevent the backup of distributed material into the dispensing nozzle/system during shutdown, and advantageously a control for the automatic regulation of the starting and stopping of the dispensing function.

17 Claims, 2 Drawing Sheets

BACKUP-PROOF FLUID DISTRIBUTION APPARATUS

BACKGROUND OF THE INVENTION

Field of the Invention

The present invention relates to apparatus for the distribution of fluid materials, notably somewhat caustic liquid materials, such as essential oils, oils and perfumes.

SUMMARY OF THE INVENTION

A major object of the present invention is the provision of fluid distribution apparatus comprising a nozzle, the geometry and mode of operation of which prevent the return, back into the nozzle, of the fluid materials injected into a given distribution system for transporting/treating such materials. Thus, any corrosion or deterioration of the nozzle that might be occasioned by a backup of such materials is conveniently avoided.

Another object of this invention is the provision of fluid distribution apparatus comprising an anti-backup nozzle and means for regulating the starting and stopping of the distribution of fluid material into a system as a function of the longevity of particles of such fluid material in the medium in which they are distributed.

Another object of this invention is the provision of fluid distribution apparatus comprising means whereby distribution of fluid material is predetermined, which means include a preset electronic control module adopted for such automatic pre-established starting and stopping. Such means in and of itself comprises a self-regulating electronic control module.

Briefly, and with reference to the attached FIG. 1 of the Drawings, the apparatus according to the present invention comprises a container 7 for the fluid material to be distributed, a system E for transporting such fluid through a nozzle 5 and a system C for controlling the transport system, and wherein the nozzle 5 comprises a central orifice 5b connected to an initiator of flow of a carrier fluid 3, a head 5a defining, together with the central orifice 5b, a cavity 14 over a portion of the length of said central orifice 5b, which cavity is intended for conveying the carrier fluid and includes at least one port 15, and said nozzle including at least one lateral duct 6, arranged parallel to the central duct 5b, extending at one end into the fluid to be distributed and terminating at the other end substantially at the level of the corresponding port 15.

DETAILED DESCRIPTION OF THE PREFERRED EMBODIMENTS OF THE INVENTION

Figure 1:
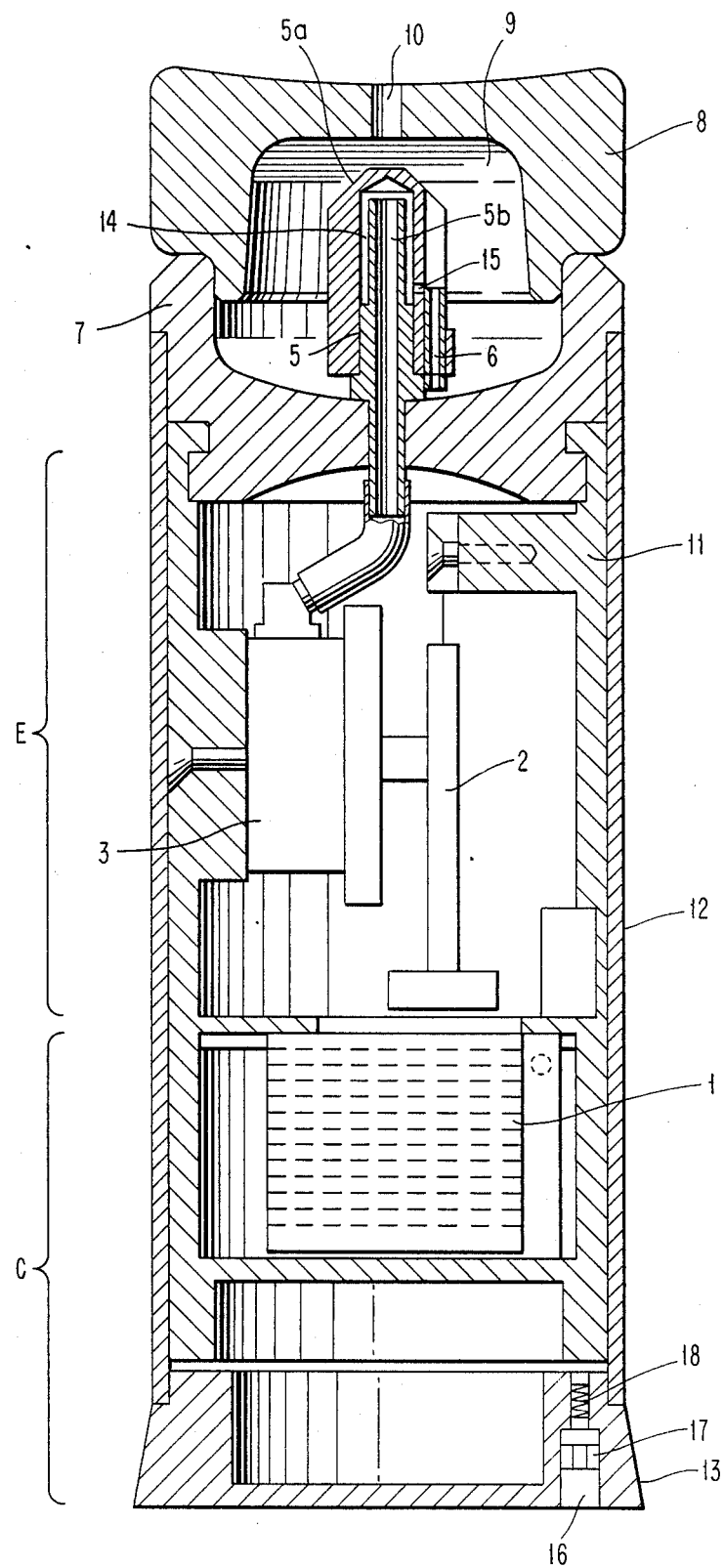
FIG. 1 is a cross-sectional view of suitable dispensing apparatus according to the invention.

More particularly according to the present invention, the end of the lateral duct or ducts 6 opposite the port or ports 15 is preferably bevelled. Advantageously, the angle formed by the bevel plane with the axis of the duct 15 ranges from 30° to 80°.

The lateral duct or ducts 6 can advantageously be accommodated partly in the head 5a and communicate substantially at the level of the ports 15 at the base of a cut out formed in said head in the extension of the said ducts.

The lateral duct or ducts 6 can be secured, for example by bonding, to the head 5a or the central duct 5b or to the container 7, or even to the cap 8, as more fully discussed below.

In the apparatus of the invention, the transport system E for the fluid to be distributed comprises a generator for initiation of flow of the carrier fluid, advantageously a pump 3 connected to a source of the carrier fluid, an element 4 for connection to the central duct 5b, the pressure delivered by the pump and the dimensioning of the connecting device to the central duct being arranged to establish a sufficiently low pressure in the lateral duct or ducts 6 to convey the fluid to be distributed.

The low pressure thus obtained causes the fluid to be distributed to be drawn in through the lateral duct 6 to the base of the container 7. The column of fluid thus obtained is broken at the level of the end of the duct 6 corresponding to the port 15, and in particular when the end of said duct is bevelled, thus effecting dispersion of particles of the fluid and the diffusion thereof. In a preferred embodiment of the invention, this diffusion is firstly effected in a preparation chamber 9 formed by placing a cap 8 above the container 7 and around the nozzle 5 before ejection through at least one opening 10 provided at the top of such cap. The location of the opening or of several openings and their dimensions are easily determined by one skilled in this art, taking into account, in particular, the dimensions of the fluid particles diffused, as well as their susceptibility to being diffused, inhaled or deposited.

In another preferred embodiment of the invention, the cap 8 has a substantially cylindrical shape at the end corresponding to the container and the other end of which is constituted by a bi-concave surface perforated at its center, the said bi-concave shape making it possible to orient the diffusion of the fluid and at the same time to recycle the diffused fluid which may have been redeposited on the said cap.

The presence of the cavity 14 in the nozzle in accordance with the invention makes it possible to trap the fluid material during the period of stoppage of the carrying system, thus preventing the return of the fluid into the transport system and the risk of deterioration of said system.

The head 5a can be fixed to the central duct 5b, for example, by screwing or bonding.

The carrier fluid for the fluid to be distributed is advantageously constituted by the air surrounding the apparatus. The air can penetrate into the apparatus, for example through an opening 16 situated at the base 13 of the apparatus, and depending on the state of the surrounding air, it may be advantageous to cause this air to pass through a filtering device 18 before supplying the generator E of the carrier fluid. This air can also be dried and/or reheated by a heater or drying element 17.

The apparatus of the invention also comprises a control system C for the system transporting the fluid.

This control system comprises means for starting and stopping the generator of the fluid carrier. More precisely, this system comprises means for regulating the frequency of starting and stopping the generator according to the concentration of the fluid diffused into the surrounding medium.

These regulating means advantageously comprise an electronic system timing the switched off stages of the system and the operating stages of the said system, it being possible for several switched off stages and/or several operating stages to have different durations. This same electronic system also permits variable values to be selected for the rate of flow of the fluid to be distributed. Because of this, one may select operating stages of different durations, with variable flow rates interrupted by switched off stages which are also of different durations, all of these duration/flow rate combinations being possible and determinable according to the diffused fluid and in particular its density, projection pressure and the active volume wherein the fluid is distributed.

The power supply for the device can be provided by a simple electric connection on 110/120 volts a.c., 50/60 hertz or at a low voltage, it being possible to control the activation or final turning off by a simple switch or a remote control system which can also actuate the various timing stages.

The starting and stopping of the carrier system can be controlled by the electronic system, for example, by starting an electromagnet 1 controlling the generator 3 of the carrier fluid, either directly or by means of an activating arm 2.

Figure 2:
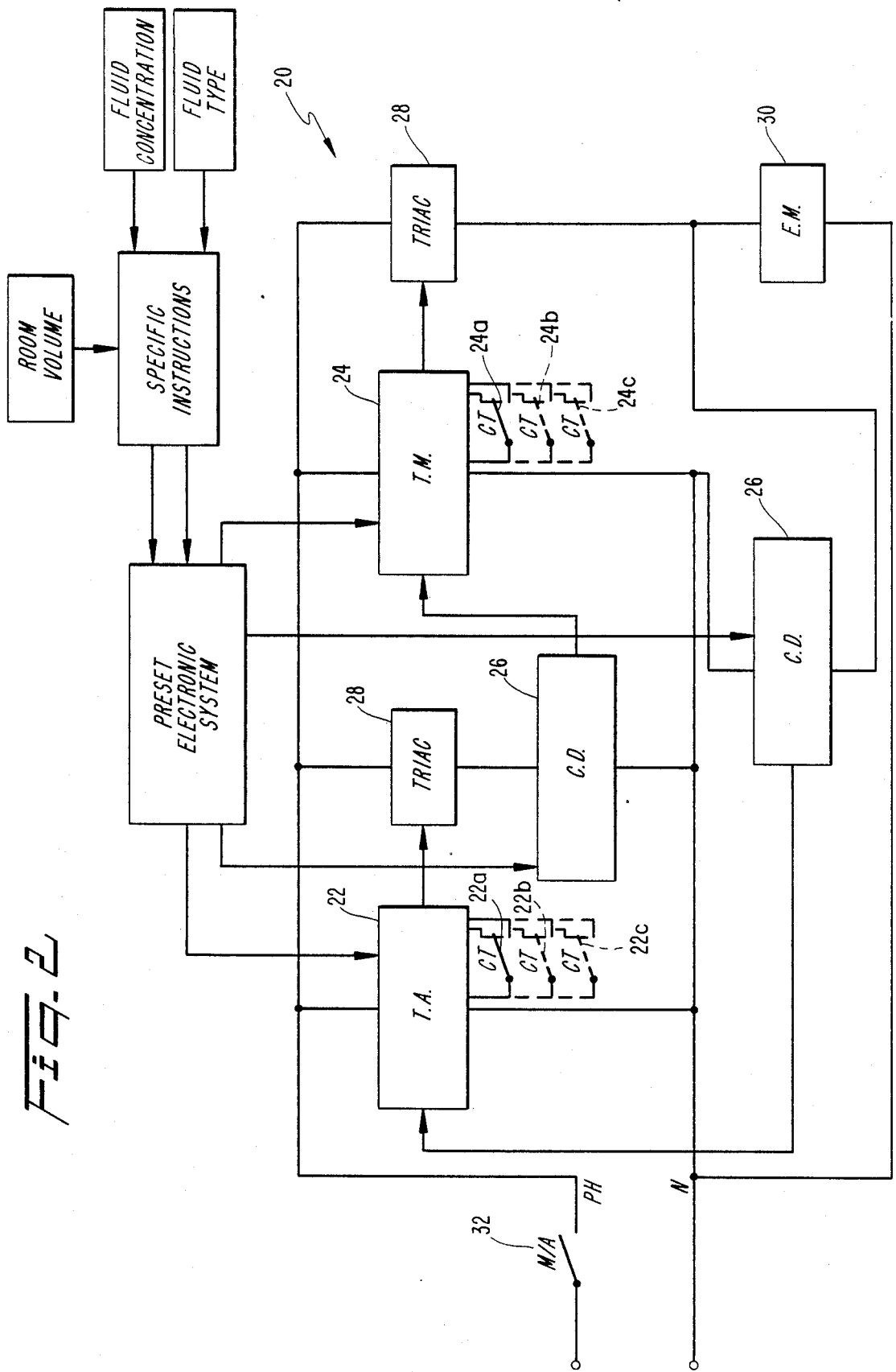
FIG. 2 is a circuit diagram of the electronic system for regulating the starting and stopping of the dispensing function according to the invention.

The electronic system for regulating the frequency of the starting/stopping stages and, if necessary, the rate of flow of the distributed fluid can be preset before being installed in the apparatus, taking into account the nature of the fluid to be distributed and the medium into which it will be projected. FIG. 2 illustrates a circuit diagram 20 appropriate for such purpose. In this Figure, the symbols have the following meanings: TA=timing circuit 22 for stoppage; TM=timing circuit 24 for operative period; CD=starting circuit 26; TRIAC=static switch 28; CT=connections for timing of stoppage stages at *22a*, *22b* and *22c*; and for operative period stages at *24a*, *24b* and *24c*; EM=electromagnet 30; M/A=operation/stoppage switch 32; PH=phase; N=neutral; S=mains.

The timing connections correspond to different timing values, both as regards operation and stoppage.

This system can also comprise a plurality of possibilities for timing the operating/stoppage stages and if necessary, for the flow rate values and can be controlled by introducing specific instructions, for example by means of punched cards or magnetic cards corresponding to [various] distributed fluid/carrier medium pairs.

In another embodiment of the invention, the electronic control system is self-regulating. For this purpose, this system comprises data input means concerning at least the fluid to be distributed and the volume wherein this fluid will be projected, means for analyzing the said data and for determining the concentration of the fluid in this medium and means for starting the carrier system according to the concentration.

The apparatus of this invention is advantageously contained in a unit of shell 12 and insulating body 11, thus providing safety by double insulation.

The apparatus of the present invention permits the distribution of various liquids such as essential oils, pleasing perfume based products, deodorants, medicinal substances, insecticides, and the like.

The apparatus of this invention is particularly useful because of its potential for distributing an amount of product adapted to the medium wherein it will be transported. Moreover, because of its construction, it protects the apparatus against the risks of deterioration and corrosion by preventing the return of the product to be diffused from the moment the carrier system is terminated. Thus, it is particularly suitable for the distribution of substances of the classes mentioned above and which prove to be particularly reactive with those materials generally used for the manufacture of diffusion apparatus, such as metals, plastics, rubber, and the like.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. Apparatus for distributing a liquid material entrained within a carrier medium therefore, which comprises a container for such liquid material, means for entraining the fluid material within the carrier medium and an anti-back-up nozzle dispenser therefore, and control means for controlling the flow of the carrier medium, said nozzle dispenser comprising a central duct outlet communicating with an initiator of flow of the carrier medium, at least one lateral duct conduit parallel to said central duct outlet, and a head member defining, together with said central duct outlet a cavity coaxial with said central duct outlet along a portion of the length thereof, said cavity being adapted for the passage of carrier medium therein, said cavity including at least one port opening communicating with the at least one lateral duct conduit comprising said nozzle dispenser, said cavity connected to said central duct at an end of said cavity distal to said at least one port opening, and said at least one lateral duct conduit being adapted at its lower end to extend into the liquid material to be distributed and substantially communicating at its upper end with said at least one port opening.

2. The distribution apparatus as defined by claim 1, wherein the end of said at least one lateral duct conduit proximate the at least one port opening is bevelled to an angle of from 30° to 80°.

3. The distribution apparatus as defined by claim 1, wherein said at least one lateral duct conduit is integral with said head member.

4. The distribution apparatus as defined by claim 1, wherein said at least one lateral duct conduit is integral with said central duct outlet.

5. The distribution apparatus as defined by claim 1, wherein said at least one lateral duct conduit is integral with said container.

6. The distribution apparatus as defined by claim 1, wherein said means for entraining the liquid material within a carrier medium comprises pump means for pumping carrier medium through the central duct outlet and for establishing a sufficiently low pressure in the at least one lateral duct conduit as to permit the transport of the liquid material therethrough.

7. The distribution apparatus as defined by claim 1, comprising a cap element surmounting said container and nozzle dispenser, defining a chamber adapted to confine the entrained liquid material for distribution, and said cap element comprising at least one outlet of distribution.

8. The distribution apparatus as defined by claim 1, comprising means for utilizing the atmosphere surrounding said apparatus as the carrier medium.

9. The distribution apparatus as defined by claim 8, comprising means for at least one of filtering and heating the surrounding atmosphere to be used as the carrier medium.

10. The distribution apparatus as defined by claim 1, comprising means for automatically starting and stopping the flow of the carrier medium.

11. The distribution apparatus as defined by claim 10, wherein said means for automatically starting and stopping the flow of the carrier medium is responsive to the concentration of the fluid material entrained in said carrier medium.

12. The distribution apparatus as defined by claim 10, comprising at least one starting timing means and at least one stopping timing means.

13. The distribution apparatus as defined by claim 10, said means for automatically starting and stopping the flow of the carrier medium also regulating the distribution of the liquid material.

14. The distribution apparatus as defined by claim 10, wherein said means for automatically starting and stopping the flow of the carrier medium initiates the starting and stopping at predetermined times.

15. The distribution apparatus as defined by claim 10, wherein said means for automatically starting and stopping the flow of the carrier medium operates in response to a plurality of timing sequences, each said timing sequence being responsive to specific operator instructions.

16. The distribution apparatus as defined by claim 11, said means for automatically starting and stopping the flow of the carrier medium comprising data input means responsive to the liquid material to be distributed and the volume wherein it is to be introduced, means for analyzing such data and for determining the concentration of the liquid material in the carrier medium and means for starting the flow of the carrier medium in response to said determined concentration.

17. The distribution apparatus as defined by claim 16, said data input means including at least the density and dispensing pressure of the liquid material.

* * * * *